(12) United States Patent
Miller

(10) Patent No.: US 11,975,180 B2
(45) Date of Patent: *May 7, 2024

(54) NEEDLE STICK PROTECTION DEVICE

(71) Applicant: Stuart H Miller, Landing, NJ (US)

(72) Inventor: Stuart H Miller, Landing, NJ (US)

(73) Assignee: MILLER MEDICAL LLC, Randolph, NJ (US)

( * ) Notice: Subject to any disclaimer, the term of this patent is extended or adjusted under 35 U.S.C. 154(b) by 705 days.

This patent is subject to a terminal disclaimer.

(21) Appl. No.: 17/036,625

(22) Filed: Sep. 29, 2020

(65) Prior Publication Data
US 2021/0023311 A1    Jan. 28, 2021

Related U.S. Application Data

(62) Division of application No. 15/947,121, filed on Apr. 6, 2018, now Pat. No. 10,828,426.

(51) Int. Cl.
*A61M 5/32* (2006.01)
*A61M 5/50* (2006.01)
*A61M 5/162* (2006.01)

(52) U.S. Cl.
CPC ........ *A61M 5/3216* (2013.01); *A61M 5/3202* (2013.01); *A61M 5/50* (2013.01); *A61M 5/1626* (2013.01); *A61M 2005/3217* (2013.01); *A61M 2005/3247* (2013.01)

(58) Field of Classification Search
CPC .............. A61M 5/3216; A61M 5/3205; A61M 5/1626; A61M 5/50; A61M 2005/3247; A61M 2005/3217
See application file for complete search history.

(56) References Cited

U.S. PATENT DOCUMENTS

| | | | |
|---|---|---|---|
| 4,982,842 A | 6/1991 | Hollister | |
| 5,150,089 A | 9/1992 | Kirk, III et al. | |
| 5,151,089 A * | 9/1992 | Kirk, III | A61M 5/3216 604/263 |
| 5,509,907 A * | 4/1996 | Bevilacqua | A61M 5/3216 604/263 |
| 10,828,426 B2 * | 11/2020 | Miller | A61M 5/3216 |
| 2014/0052072 A1 * | 2/2014 | Simas, Jr. | A61M 5/3216 29/428 |
| 2015/0283332 A1 * | 10/2015 | Woehr | A61M 5/3202 221/26 |
| 2017/0258990 A1 * | 9/2017 | Wei | A61M 5/3216 |
| 2018/0353707 A1 * | 12/2018 | Wei | A61M 5/321 |
| 2020/0046276 A1 * | 2/2020 | Valentino | A61M 5/3216 |

* cited by examiner

*Primary Examiner* — Nathan R Price
*Assistant Examiner* — Anh Bui
(74) *Attorney, Agent, or Firm* — Welsh Flaxman & Gitler LLC

(57) ABSTRACT

A needle stick protection device includes a distal shield member having a slot which allows a needle to freely pass between shielded and unshielded positions an infinite number of times. The needle stick protection device also includes a proximal base member and a hinge connecting the distal shield member to the proximal base member. A locking mechanism secures the proximal base member to the distal shield member. The locking mechanism includes a compressive sleeve of the distal shield member and a distal cylindrical collar of the proximal base member, which frictionally fit together in a manner securing the proximal base member and the distal shield member.

14 Claims, 20 Drawing Sheets

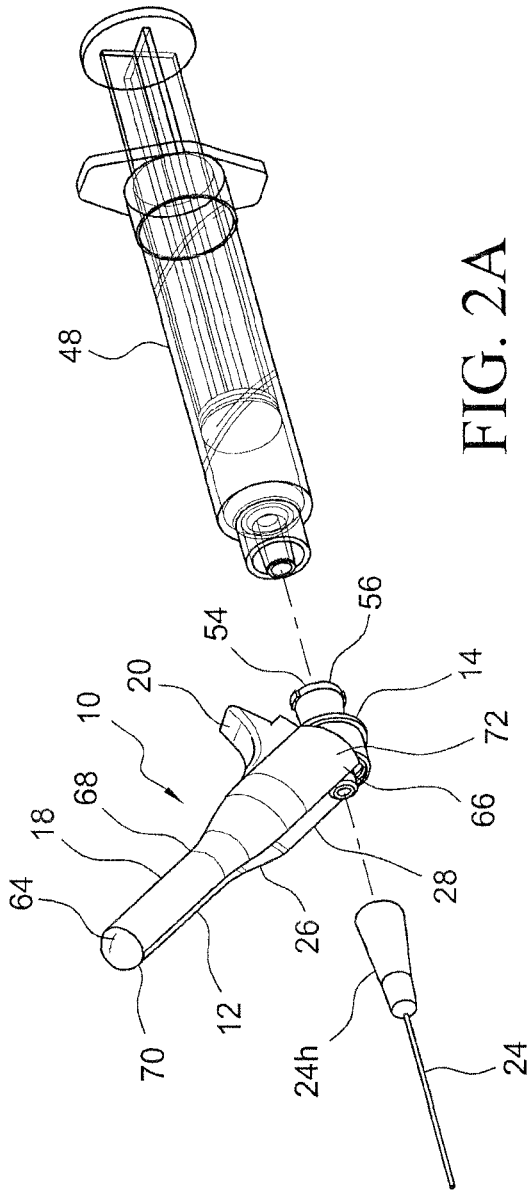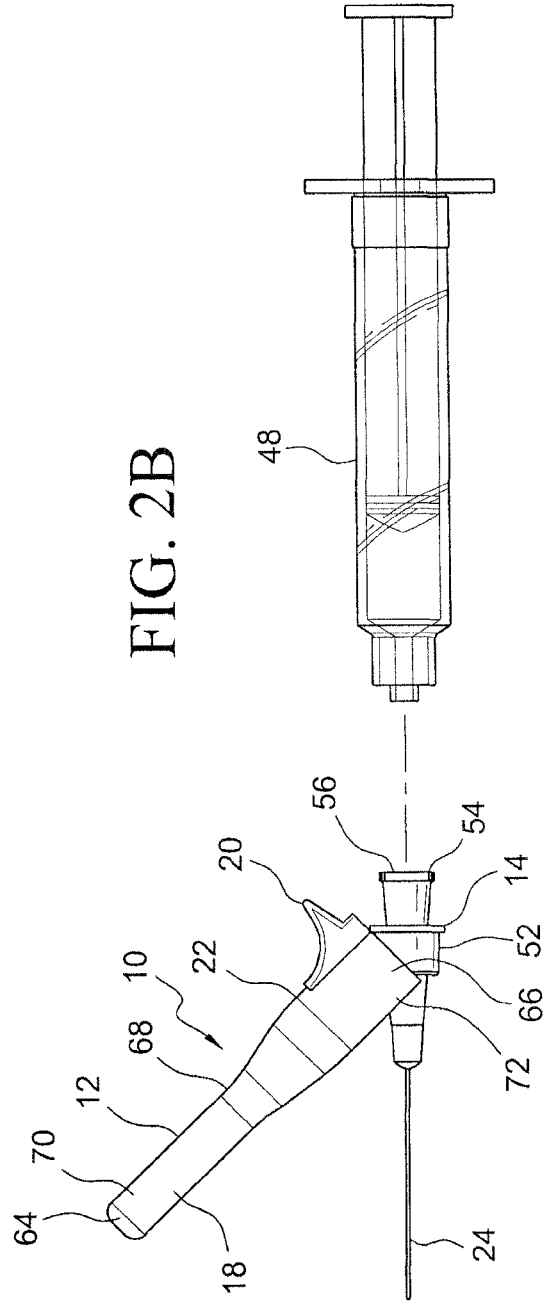

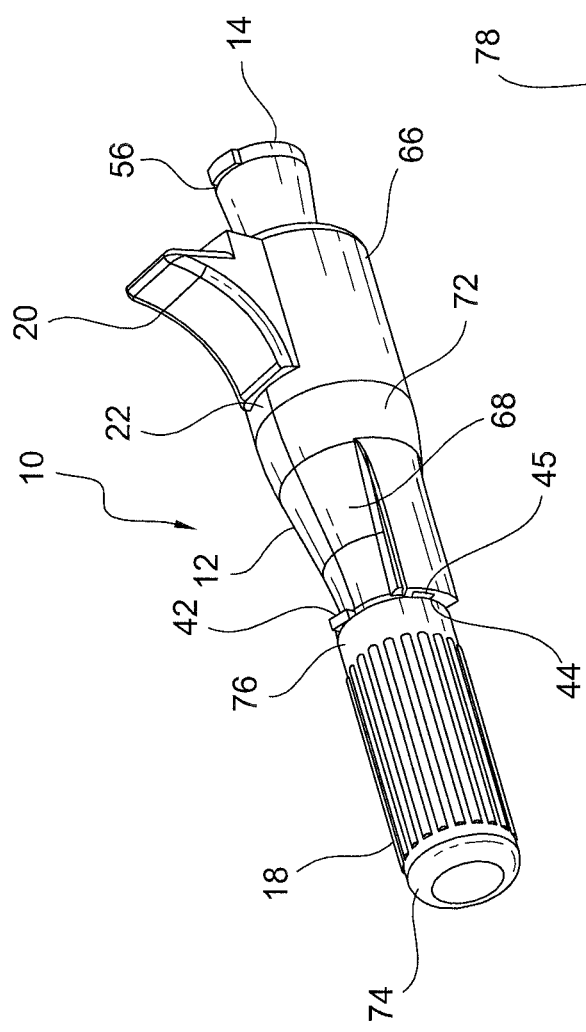
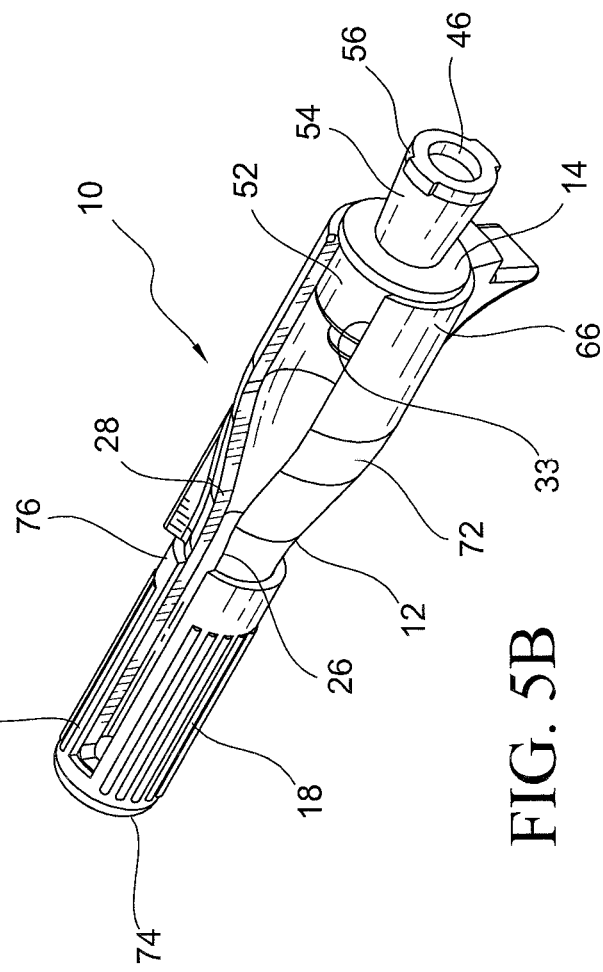
FIG. 5A
FIG. 5B

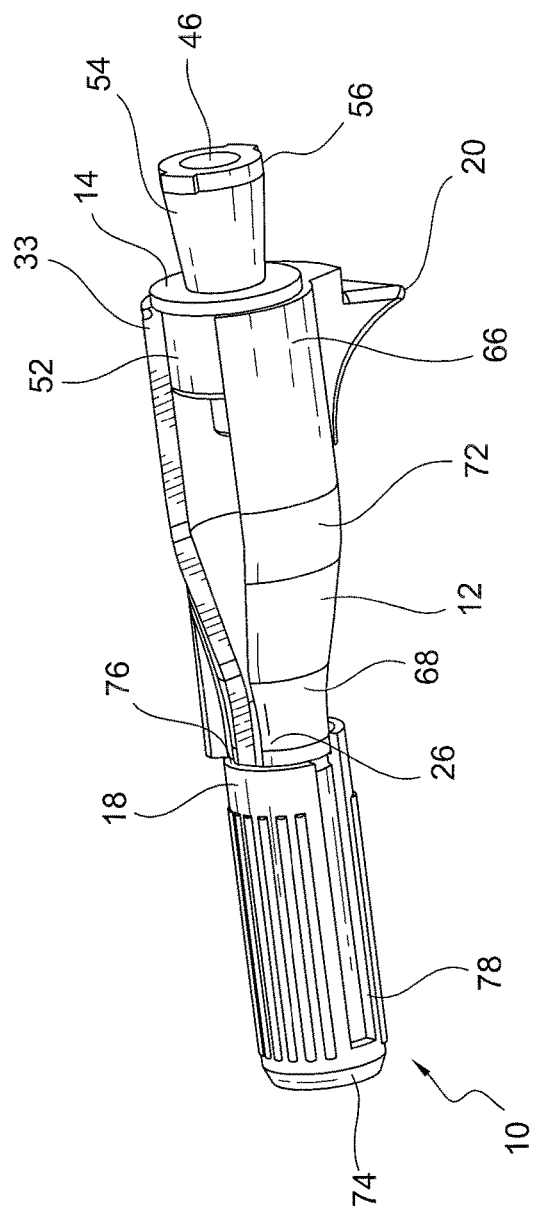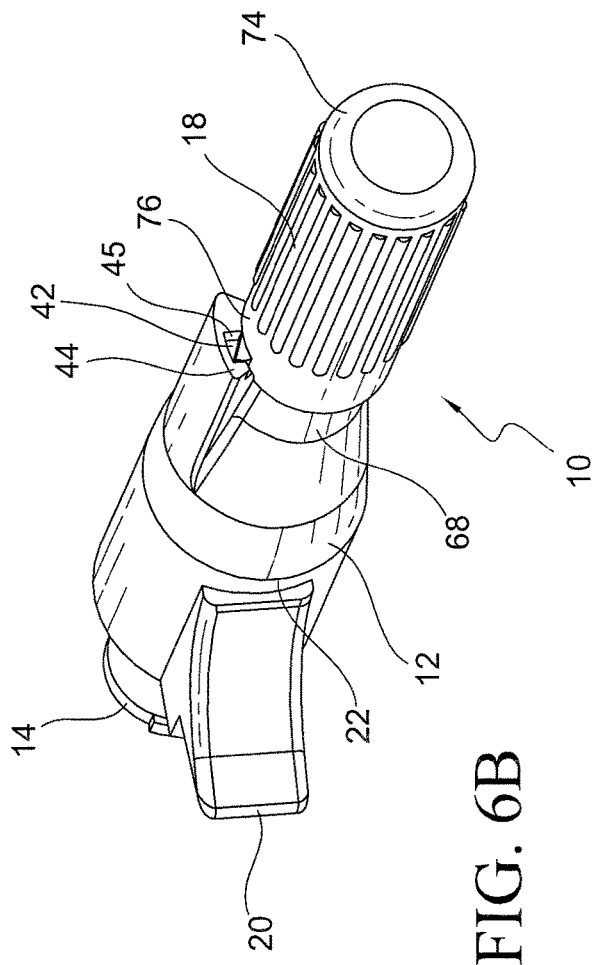
FIG. 6A
FIG. 6B

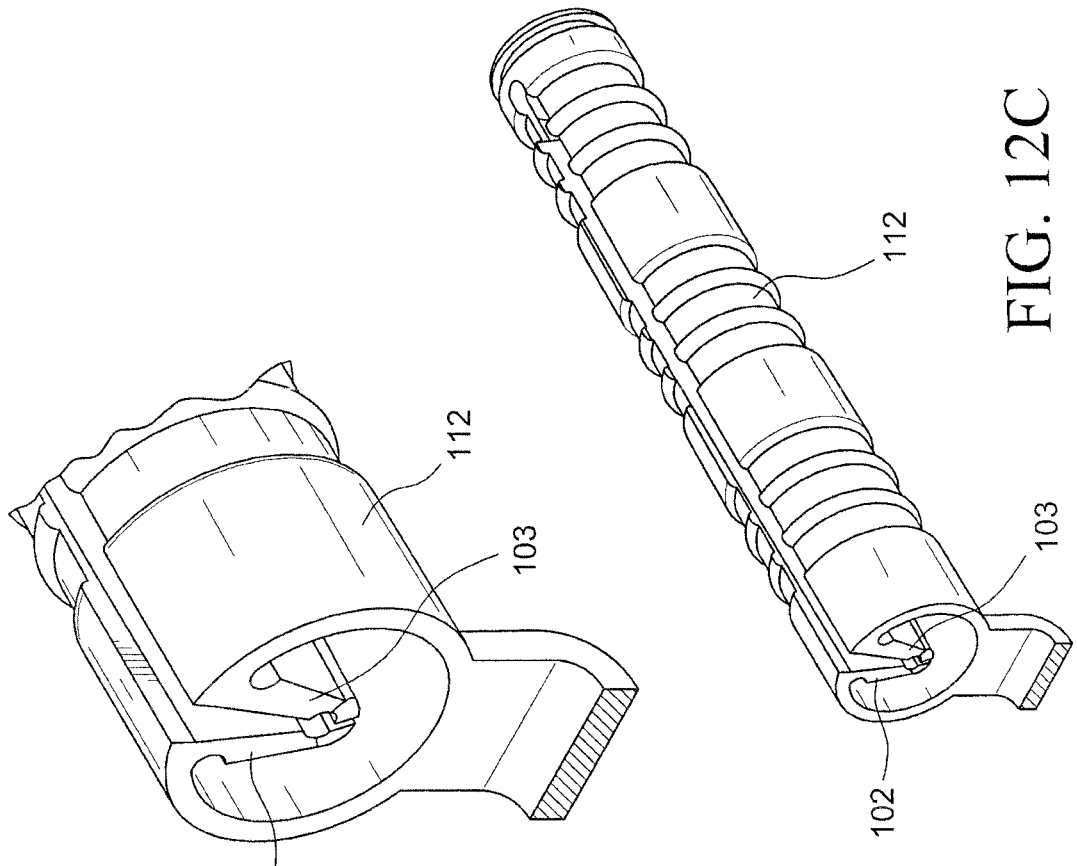
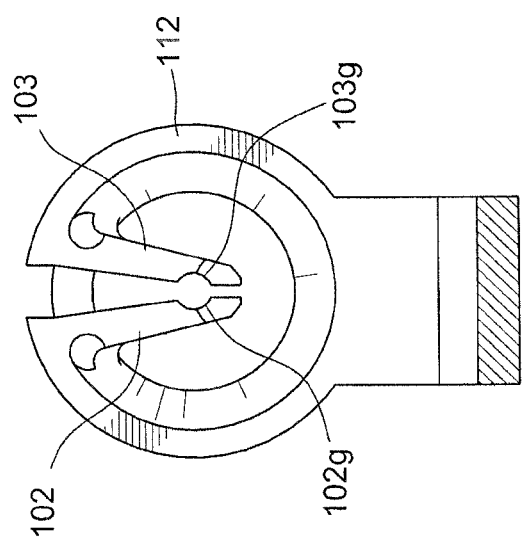

NEEDLE STICK PROTECTION DEVICE

CROSS REFERENCE TO RELATED APPLICATION

This application is a division of U.S. patent application Publication Ser. No. 15/947,121, entitled "NEEDLE STICK PROTECTION DEVICE," dated Apr. 6, 2018, which is currently pending.

BACKGROUND OF THE INVENTION

1. Field of the Invention

The invention relates to a device for prevention of needle stick injuries. Precisely, this invention relates to a device that protects the operator from needle stick injuries by actively, selectively locking and unlocking the device, then permanently locking the device for disposal.

2. Description of the Related Art

Various patented devices are known for shielding and unshielding hypodermic needles that are being utilized by medical personnel during a medical procedure on a given patient. The various devices all achieve a similar goal, but act by different mechanisms. Ultimately, the device selected by medical personnel comes down to personal preference by the operator.

The Applicant, as well as most medical personnel involved in the use of hypodermic needles, are well aware of the extremely dire potential consequences of injury by a contaminated hypodermic needle. While known diseases such as Hepatitis B, C, & D, HIV, and AIDS are well known documented sequelae, others such as Zika and other infectious diseases can also be spread by a contaminated needle stick. While most needle stick injuries go unreported, millions of needle stick injuries occur each year in the United States, with a cost not only of lost work, but financial consequences costing more than hundreds of millions of U.S. dollars per annum.

This lack of protection for needle stick injuries is largely ignored by medical personnel, manufacturers, as well as the government. The misleading belief that needle stick injuries are prevented by currently-available devices results in a false sense of security by medical personnel, and a prejudice by manufacturers to create devices similar to those currently available in the United States and abroad. In fact, all currently available needle stick protection devices available for the United States market lock onto the needle to prevent its use, only prior to being disposed. During a procedure, once a sterile needle is placed into a patient and is subsequently considered contaminated, the transfer of said contaminated needle from medical personnel, or even one person grasping the unprotected, contaminated needle from the sterile field, often results in needle stick injury.

The above proves the necessity for a device to shield a contaminated hypodermic needle during a procedure to protect medical personnel from potentially-deadly complications associated with needle stick injuries.

SUMMARY OF THE INVENTION

It is, therefore, an object of the present invention to provide a needle stick protection device including a distal shield member having a slot which allows a needle to freely pass between shielded and unshielded positions an infinite number of times. The needle stick protection device also includes a proximal base member and a hinge connecting the distal shield member to the proximal base member. A locking mechanism secures the proximal base member to the distal shield member. The locking mechanism includes a compressive sleeve of the distal shield member and a distal cylindrical collar of the proximal base member, which frictionally fit together in a manner securing the proximal base member and the distal shield member.

It is another object of the present invention to provide a needle stick protection device including a distal shield member including a slot which allows a needle to freely pass between shielded and unshielded positions. The distal shield member further includes a distal rotating shield adapted for rotation and locking to prevent further use of the needle stick protection device, whereby rotation of the distal rotating shield selectively blocks the slot that allows passage of the needle in and out of the needle stick protection device. The needle stick protection device also includes a proximal base member and a hinge connecting the distal shield member to the proximal base member.

It is a further object of the present invention to provide a needle stick protection device including a distal shield member having a first end and second end. The distal shield member further includes a shield actuating tab positioned adjacent the second end of the distal shield member and a slot which allows a needle to freely pass between shielded and unshielded positions. The needle stick protection device also includes a proximal base member including a first end and a second end, and a hinge connecting the second end of the distal shield member to the first end of the proximal base member, wherein the shield actuating tab includes a first end and second end, and the second end of the shield actuating tab includes a cutout section that allows additional range of motion of the distal shield member relative to the proximal base member. The needle stick protection device is removed from the needle by the application of downward force by the thumb on the shield actuating tab, causing the distal shield member to swing downward and away from the needle and to shield the needle stick protection device to protect the operator from needle stick injuries the thumb pushes up on the raised shield actuating tab until the proximal base member and the distal shield member abut.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 2A and 2B respectively show an exploded view revealing the steps required for connecting the hypodermic needle to the needle stick protection device via the Luer connection, and a side view prior to connecting the needle stick protection device to the syringe.

FIGS. 5A and 5B are respectively a top perspective view and a bottom perspective view illustrating the distal rotating lock shield with the needle stick protection device in the "safe" reusable position.

FIGS. 6A and 6B are respectively first and second perspective views of the needle stick protection device illustrating the distal rotating lock shield in the permanently locked position.

FIGS. 8A, 8B, 9, 10, 11, 12A, 12B, and 12C illustrate an alternative embodiment in which the needle is captured between 2 cantilevered beams. The needle passes from Position 1 (where it is not shielded), to Position 2 (where it is shielded), and ultimately to Position 3 (where it is rendered irreversibly locked out). FIGS. 8A and 8B are respectively is a cross sectional view of a square shaped distal shield member 12 and a detailed view along the section 8B embodying this alternative embodiment. FIGS. 9 and 10 are respectively a perspective view and a side partial cross sectional view of a needle stick protection device with a cylindrical shaped distal shield member (shown in cross section with the needle between the cantilevered beams despite the needle shield collar being rotated relative to the distal shield member to its open position) in accordance with another version of an embodiment including two cantilevered beams, and FIG. 11 is a cross section view along the line 11-11 in FIG. 10. FIGS. 12A, 12B, and 12C are respectively an end view, a detailed perspective view and a perspective view of another version of cylindrical shaped distal shield member including two cantilevered beams.

FIGS. 13 to 15 are respectively a side view in the safe position (with the needle not shown), a side view in the open position, and a detailed perspective view in the safe position.

FIG. 17 is a perspective view of the needle shield collar in accordance with a first alternative embodiment, FIGS. 18A and 18B are axial views of alternative embodiments of the needle shield collar, wherein FIG. 18A is an axial view of the embodiment shown in FIG. 17.

FIGS. 19A and 19B arc respectively perspective views of the lower portion of distal shield member in alternative embodiment, wherein the embodiment shown in FIG. 19A is adapted to work in conjunction with the needle shield collar of FIG. 18A and the embodiment shown in FIG. 19B is adapted to work in conjunction with the needle shield collar of FIG. 18B.

DESCRIPTION OF THE PREFERRED EMBODIMENTS

Figure 1B:
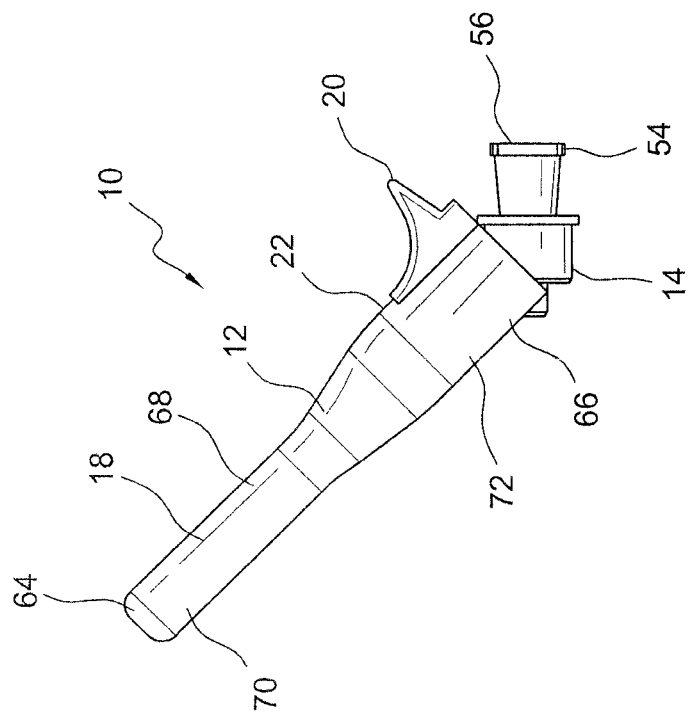
FIGS. 1A and 1B are respectively a perspective view and a side elevation view of the needle stick protection device of the present invention showing the Luer connection and the hub member. The needle stick protection device is shown in the open, or "ready to use" position.
Figure 1A:
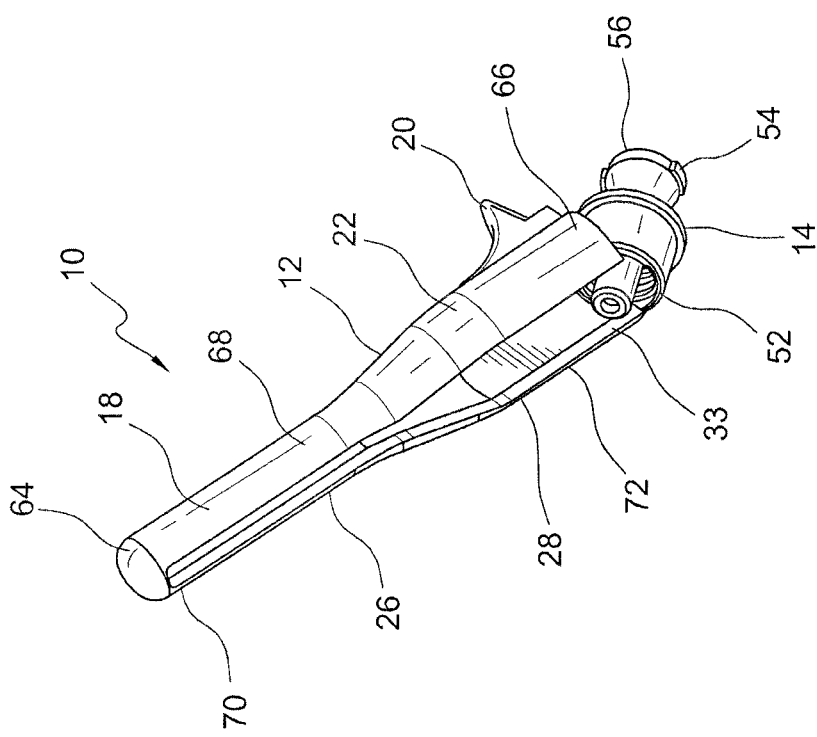
Figure 3:
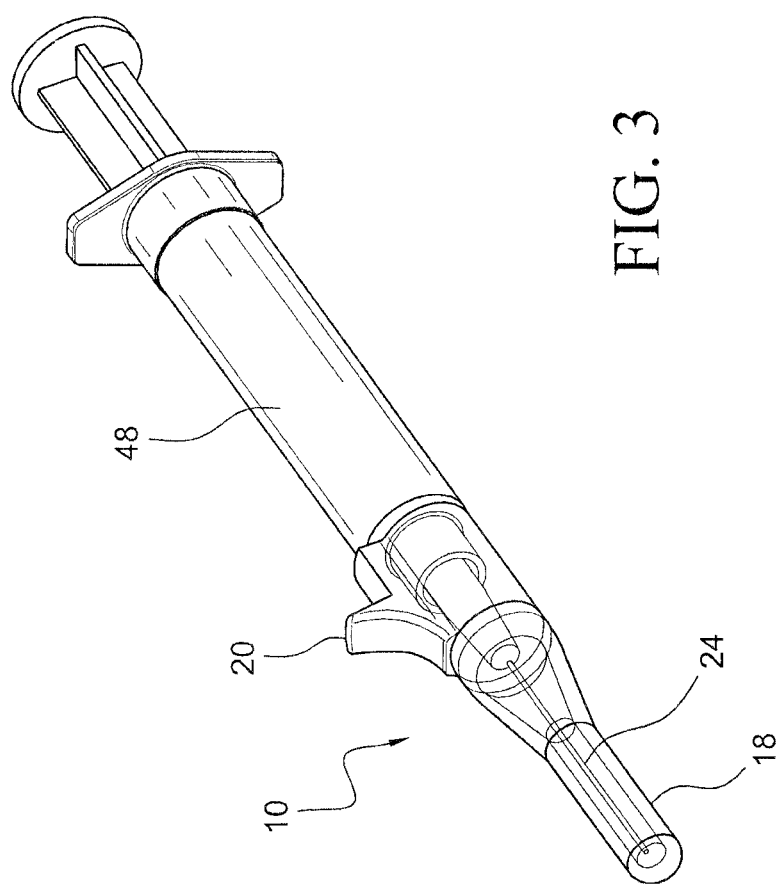
FIG. 3 is a perspective view showing the needle stick protection device connected to a syringe. The needle stick protection device is in a "safe" position in this image.
Figure 4A:
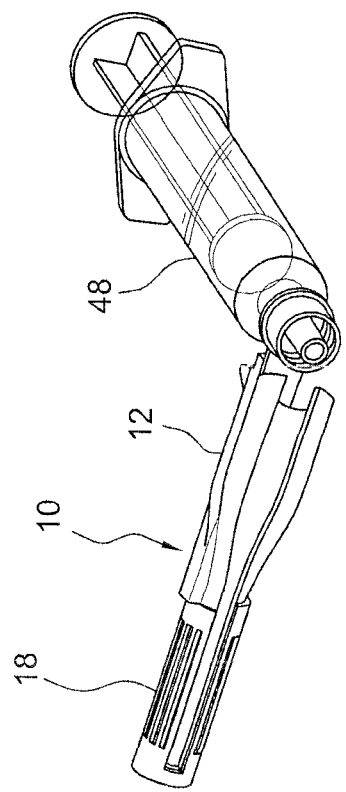
FIGS. 4A and 4B are respectively a perspective view and a side elevation view of the needle stick protection device in the "open" and ready to use position.
Figure 4B:
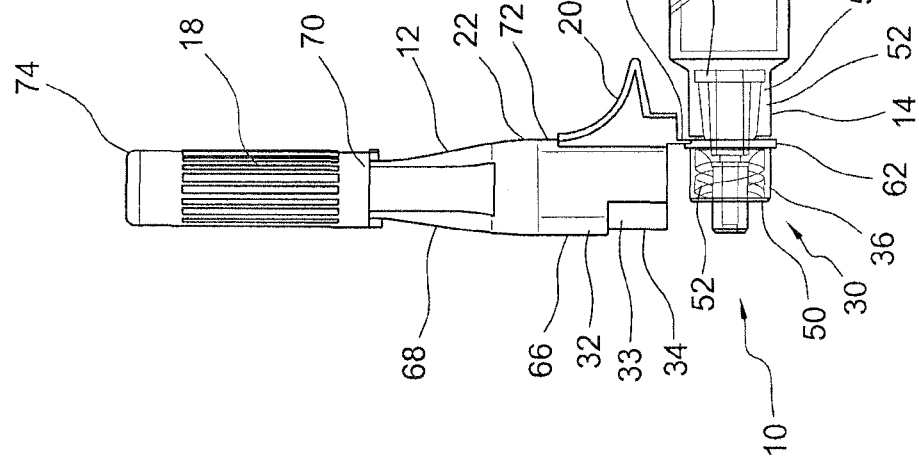

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 6, a needle stick protection device 10 is disclosed. As will be appreciated based upon the following disclosure, the needle stick protection device 10 is described as including a swinging arm mechanism that can be safely locked and unlocked an infinite number of times during a procedure by medical personnel, before locking it for the final time prior to its safe, protected disposal.

The swinging arm, or distal shield member 12, is connected to the proximal base member, or needle shield collar 14, by way of a living hinge type of connection. The hinge, in particular, a living hinge 16, connects the first end 50 of the proximal base member 14 to the second end 66 of the distal shield member 12. The needle stick protection device 10 somewhat resembles the ubiquitous needle cap that comes attached to all needles sold in the United States. However, the present needle stick protection device 10 is slightly larger than a currently available cap, in that it is composed of two distinct parts connected by a living hinge 16, as well as a brightly colored rotating lock shield 18. The present needle stick protection device 10 further includes a shield actuating tab 20 placed on the lower portion 22 of the distal shield member 12 adjacent the second end 68 of the distal shield member 12 to assist in one finger use of the needle stick protection device 10. The shield actuating tab 20 is an outwardly extending projection shaped and dimensioned for engagement by the finger of a user to effectuate movement of the distal shield member 12.

While currently existing caps are removed from a needle by pulling the cap in the same plane, yet in the opposite direction from the hypodermic needle tip, the present needle stick protection device 10 is removed from the needle 24 by the application of upward force by the thumb on the shield actuating tab 20, causing the distal shield member 12 to swing upward and away from the needle 24 in a clockwise, 90 degree fashion. The distal shield member 12 remains attached to the needle 24 via the living hinge 16 that attaches the distal shield member 12 to the proximal base member 14 of the needle stick protection device 10. Located on the bottom side 26 of the needle stick protection device 10, 180 degrees from the raised shield actuating tab 20 on the distal shield member 12, is a slot 28 which allows the needle 24 to freely pass between the shielded and unshielded positions. To close, or shield the needle stick protection device 10 to protect the operator from needle stick injuries, the thumb pushes down on the raised shield actuating tab 20, until the two sides, being that of the proximal base member 14 and distal shield member 12, subsequently abut, and cannot pass further.

The needle stick protection device 10 further includes a locking mechanism 30 composed of a compressive sleeve 32 at the base 34 of the distal shield member 12 and the distal cylindrical collar 36 of the proximal base member 14. The inner diameter of the compressive sleeve 32 is the same as the outer diameter of the cylindrical collar 36 of the distal portion of the proximal base member 14, resulting in a tight, frictional interference fit when the two are brought together. This represents an active locking mechanism where an endpoint is easily realized by any operator; that is, forcing the distal shield member 12 closed until it cannot be pushed any further, with tactile and auditory confirmation of a snapping sound and sensation. Through use of the present needle stick protection device 10, needles 24 can be safely placed on a sterile field for reuse, or safely passed back and forth between medical personnel during the procedure, in a safe manner.

When the procedure has been completed, and the equipment is being cleared, the distal rotating lock shield 18, which is provided in a bright color distinguishing itself from the rest of the needle stick protection device 10, is rotated and locked to prevent further use of the needle stick protection device 10. By rotating the distal rotating lock shield 18, the slot 28 on the bottom of the needle stick protection device 10 that allowed passage of the needle 24 in and out of the needle stick protection device 10 is blocked, preventing its further use. The locking is accomplished by rotating the distal rotating lock shield 18 to close off the slot 28. During rotation of the distal rotating lock shield 18, a small tab 42 formed along the surface of the distal rotating lock shield 18 is locked into a raised flange 44 formed along the first portion of the distal shield member 12.

It will be mentioned here that the needle stick protection device 10 can be used for various length hypodermic needles, and can be manufactured out of any materials currently sanctioned by the FDA. As per the manufacturer's discretion, the needle may be fitted during manufacture of the needle stick protection device 10, or can be mated to the Luer taper of a hypodermic needle by the operator at the time of the procedure.

With reference to the various figures, a multiple-use swinging arm needle stick protection device 10 is disclosed. The needle stick protection device 10 includes a distal shield member 12 and a proximal base member 14. A living hinge 16 connects the proximal base member 14 to the distal shield member 12. It is appreciated that while a living hinge is disclosed in accordance with a preferred embodiment of the present invention, the proximal base member 14 and the distal shield member 12 may be attached using various mechanisms.

The proximal base member 14 is an elongated structure including a central passageway 46 allowing for communication between a needle 24 and a syringe body 48. With this in mind, the proximal base member 14 includes a first end 50 having a Luer connection 52 (for example, a male shaped Luer connection) shaped and dimensioned for selective attachment of a needle 24 thereto. The proximal base member 14 includes a second end 54 having a hub member 56 shaped and dimensioned for selective attachment to a syringe body 48. It is noted that the hub member 56 preferably has a female shaped Luer connection. While Luer connections are disclosed herein for connection to the needle and the syringe, it is appreciated these connections may be achieved via various connection structures thus obviating the need for the Luer connections as disclosed heretofore.

Further inspection of the proximal base member 14 demonstrates the proximal base member 14 to contain the cylindrical collar 36, which abuts a cylindrical base ring 62, the two actually being different components of a single molded piece.

The distal shield member 12 is also of an elongated construction and includes a first end 64 and a second end 66. The distal shield member 12 is composed of a shield 68 shaped and dimensioned for positioning about a needle 24 in a manner that will be appreciated based upon the following disclosure. The shield 68 also includes a first end 70 and a second end 72, which substantially correspond with the first end 64 and the second end 66 of the distal shield member 12.

The shield 68 is cylindrical with a closed first end 70 and an open second end 72. The shield 68 also includes a slot 28 which extends from the first end 70 thereof to the second end 72 thereof. The slot 28 allows the shield 68 to be rotated between a position wherein the needle 24 is fully encased within the shield 68 and a position wherein the needle 24 is fully exposed based upon rotation of the distal shield member 12 relative to the proximal base member 14.

The distal shield member 12 of the needle stick protection device 10 includes a cylindrical portion referred to as the rotating lock shield 18. The rotating lock shield 18 covers the shield 68 at the first end 70 thereof. The rotating lock shield 18 is also an elongated cylindrical member with a closed first end 74 and an open second end 76. The rotating lock shield 18 also includes a slot 78 which extends from the first end 74 to the second end 76. The rotating lock shield 18 is a cylinder that is closed at its distal most portion, that is, the first end 74 thereof, and is of slightly greater diameter than of the shield 68.

The rotating lock shield 18 is press fitted over the first end 70 of the shield 68 of the needle stick protection device 10. The rotating lock shield 18 freely rotates clockwise and counterclockwise about the long axis of the distal shield member 12 of the needle stick protection device 10. In particular, the rotating lock shield 18 is press fitted onto a raised ring (not shown) on the shield 68, allowing it to freely rotate in a clockwise or counterclockwise fashion upon the shield 68.

As briefly mentioned above, the rotating lock shield 18 also contains a slot 78 that extends along its longitudinal length. The rotating lock shield 18 also contains an angled wedge 42 that is part of the base of the rotating lock shield 18, and rotates with the rotating lock shield 18. The shield 68 contains a raised flange 44 with a locking cavity 45, into which the angled wedge 42 is passed when it is desired to close off the slot 28 and ultimately lock the rotating lock shield 18 relative to the shield 68. The locking cavity 45 and angled wedge 42 perform the function of permanently locking the needle stick protection device 10, so it cannot be reused, and safely disposed of at the termination of the procedure.

A shield actuating tab 20 is positioned on the "closed" side of the distal shield member 12 adjacent the second end 72 of the shield 68 of the needle stick protection device 10. The shield actuating tab 20 facilitates one finger opening and closing of the needle stick protection device 10. The digit typically utilized for interacting with the shield actuating tab 20 is typically digit number one, or the thumb.

The first end 50 of the proximal base member 14 and second end 66 of the distal shield member 12 interact in a manner allowing for a frictional, interference fit. As mentioned above, the proximal base member 14 includes a cylindrical collar 36, which abuts a cylindrical base ring 62, the two actually being different components of a single molded piece. The distal shield member 12 of the needle stick protection device 10 is also of a cylindrical shape, which is slotted from approximately the 10 O'clock to 2 O'clock positions so as to define a compressive cylindrical sleeve 32. The compressive cylindrical sleeve 32 has an inner diameter (ID) equal to the outer diameter (OD) of the cylindrical collar 36 of the proximal base member 14. When the needle stick protection device 10 is in the closed position, the base of the outer compressive cylindrical sleeve 32 of the distal shield member 12 tightly overlies the outer walls of the cylindrical collar 36 of proximal base member 14, with the base of compressive cylindrical sleeve 32 abutting the cylindrical base ring 62. The needle stick protection device 10 is safely re-shielded, or closed, by pushing with one finger on the shield actuating tab 20 of the distal shield member 12, until the base of the compressive cylindrical sleeve 32 moves over the cylindrical collar 36 to create a "snap." The "snap" is created because the open portion 33 of the compressive cylindrical sleeve 32 is slightly smaller than the diameter of the cylindrical collar 36, and the compressive cylindrical sleeve 32 must expand slightly as it passes over the cylindrical collar 36 and then returns to its original size when it passes halfway over the cylindrical collar 36. The "snap" provides a tactile as well as aural notification of closure. In addition, the shield member 12 cannot be pushed forward any further, and the base of the shield member 12 now rests squarely upon the cylindrical base ring 62 of the proximal base member 14.

Figure 7B:
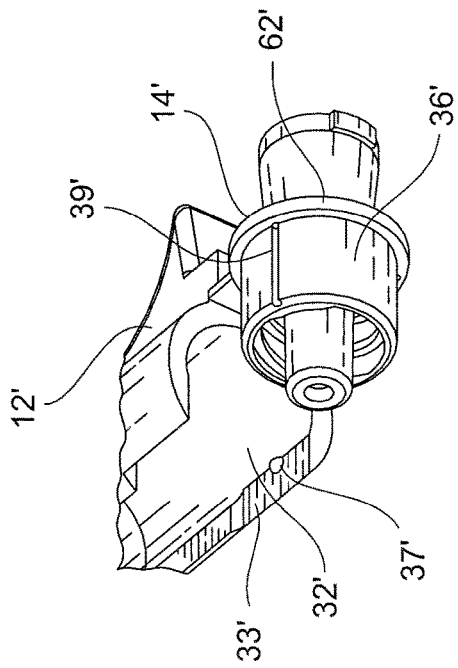
FIGS. 7A, 7B, and 7C are perspective views showing an alternative embodiment of the distal shield member and the proximal base member moved between open and closed configurations.
Figure 7C:
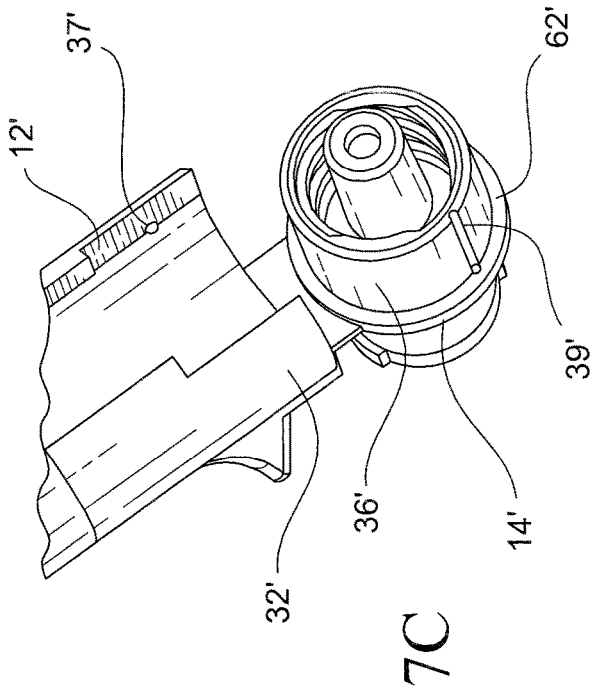
Figure 7A:
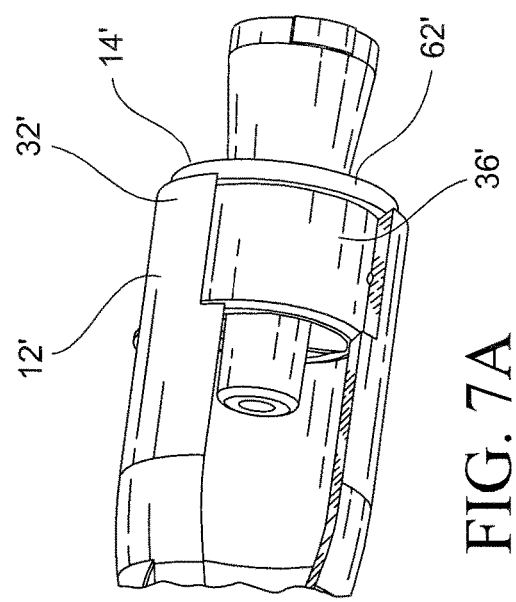

In accordance with an alternative embodiment as shown with reference to FIGS. 7A 7B, and 7C, the needle stick protection device 10' is safely re-shielded without the need for a "compressive" cylindrical sleeve. In accordance with such an embodiment, the open portion 33' of the cylindrical sleeve 32' is approximately the same size as the diameter of the cylindrical collar 36'. However, the cylindrical sleeve 32' is provided with two small raised semispherical projections (or dots) 37' at the open portion. The two small raised semispherical projections 37' are shaped and positioned to fit within female depressions 39' on the cylindrical collar 36' of the proximal base member 14' such that upon re-shielding, the two small raised semispherical projections 37' pass into the openings defined by female depressions 39' to create a "snap." The two small raised semispherical projections 37' and female depressions 39' function as two interrelated elements that interact to assist in holding the shield member 12' and the proximal base member 14' in a closed orientation. As with the prior embodiment, the "snap" provides a tactile as well as aural notification of closure. In addition, the shield member 12' cannot be pushed forward any further, and the base of the shield member 12' now rests squarely upon the cylindrical base ring 62' of the proximal base member 14'. In conjunction with such an embodiment, it is appreciated the projections and depressions could be added to the compressive cylindrical sleeve described above, but is not necessary for proper functioning of the compressive cylindrical sleeve locking mechanism; that is, the projections of this locking mechanism do not require the presence of the compressive cylindrical sleeve to function as a locking device, and can be utilized for proximal and distal portions that are not frictionally fit.

The unique and novel design of the needle stick protection device 10 is fully appreciated once its function is reviewed and understood. The present needle stick protection device 10 grew out of the need for a safety device to protect medical personnel during a procedure in which a needle 24 that has already been inserted into a patient and is contaminated, is passed among medical personnel to be reinserted into the same patient, to prevent inadvertent needle stick with a contaminated needle. An unused, sterile hypodermic needle 24 is connected by its hub member 56 to the Luer connection 52 of the proximal base member 14. The hub member 56 of the proximal base member 14 is then connected to the unused syringe body 48. The sterile, unused hypodermic needle 24 can now be used on the patient for various medical purposes, such as arterial or venous access, or administering medications, such as injectable anesthetics. The needle stick protection device 10 might also be used by dental personnel in administering anesthetics.

The living hinge 16 allows the distal shield member 12 of the needle stick protection device 10 to move 90 degrees from the axis of the hypodermic needle 24, allowing the entire length of the hypodermic needle 24 to be inserted into the patient. Thusly, the needle stick protection device 10 does not hinder nor obstruct the standard use of the hypodermic needle 24. Once the hypodermic needle 24 has been inserted into the body, it is no longer viewed as sterile or uncontaminated, and needs to be shielded to protect medical personnel. The needle stick protection device 10 can be placed in a "SAFE" position by the operator utilizing a digit, typically the thumb, to press on the shield actuating tab 20 to force the distal shield member 12 from a fully open position to the "SAFE" position where the distal shield member 12 now completely covers hypodermic needle 24. The underside of the shield 68 and the underside of the rotating lock shield 18 are slotted, allowing the hypodermic needle 24 safe and unfettered access into the protective cavity of the distal shield member 12 when the slots 28, 78 of the shield 68 and the rotating lock shield 18 are aligned. The distal shield member 12 stays in a closed, "SAFE" position covering the hypodermic needle 24 due to a tight, frictional fit of the compressive cylindrical sleeve 32 encasing the proximal cylindrical part 60 (that is, the cylindrical collar 36) of the proximal base member 14. The distal shield member 12 is stopped from further movement in the plane along the axis of the hypodermic needle 24 by a combination of interference from the base plate 62 against the base of the compressive cylindrical sleeve 32, as well as the limiting further motion by the unyielding living hinge 16. The needle-syringe assembly can now be safely passed by medical personnel without the fear of having a contaminated needle touching medical personnel's skin.

The needle 24 can then be retrieved from the sterile field, and passed to the operator, who takes the needle-syringe assembly in the "SAFE" position and, depressing on the shield actuating tab 20, can safely expose the shielded, contaminated needle for use once again, without any danger of inadvertent needle stick injury as no portion of his finger or hand comes in the vicinity of the hypodermic needle 24.

Once the procedure has been terminated, the needle stick protection device 10 can be safely "LOCKED OUT," so that it can never be used again, and the contaminated needle 24 poses no threat to anyone who is dealing with medical waste. This is easily accomplished by rotating the rotating lock shield 18 clockwise so the slot 78 of the rotating lock shield 18 and the slot 28 of the shield 68 move out of alignment, and the angled wedge 42 passes into the flange cavity 45. Once the angled wedge 42 is inside the cavity 45, the base of the wedge 42 keeps the safety shield "LOCKED OUT" due to the inability of the straight base of the wedge 42 to pass by the straight edge of the flange. The entire contaminated syringe-needle assembly can now be safely discarded as medical waste using conventional means.

In accordance with alternative embodiments as seen in FIGS. 8 to 12, as well as FIGS. 13 to 16, the needle stick protection device 110, 210 functions in a similar fashion as described in the embodiment above, with the exception that the device passes from "EXPOSED," to "SAFE," to "LOCKED OUT" positions by moving the needle between various positions relative to internal cantilevered beams located within the distal shield member of the needle stick protection device, which directly act upon the hypodermic needle. Each of these two embodiments will be discussed in detail.

Figure 8A:
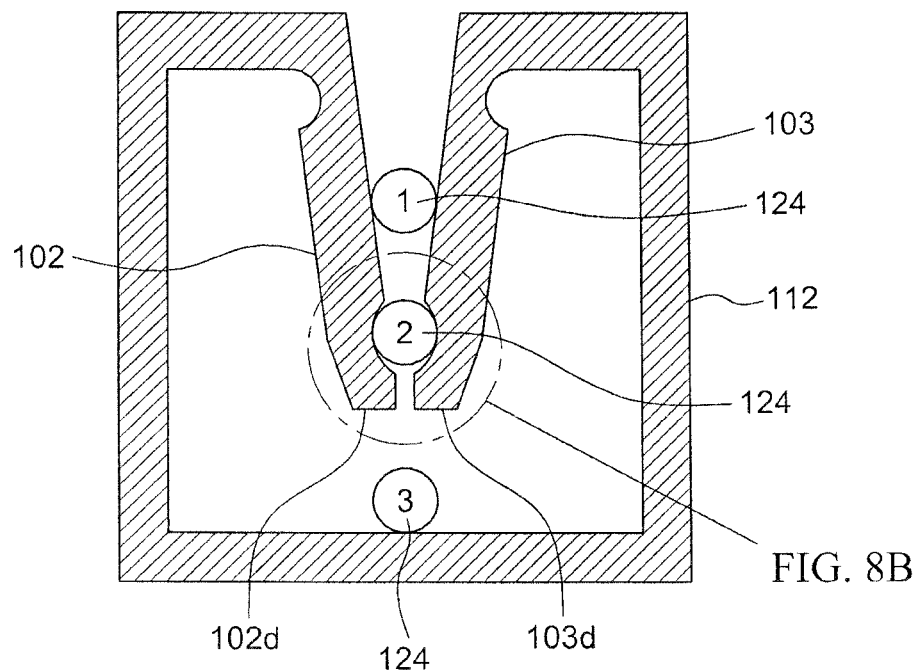
Figure 8B:
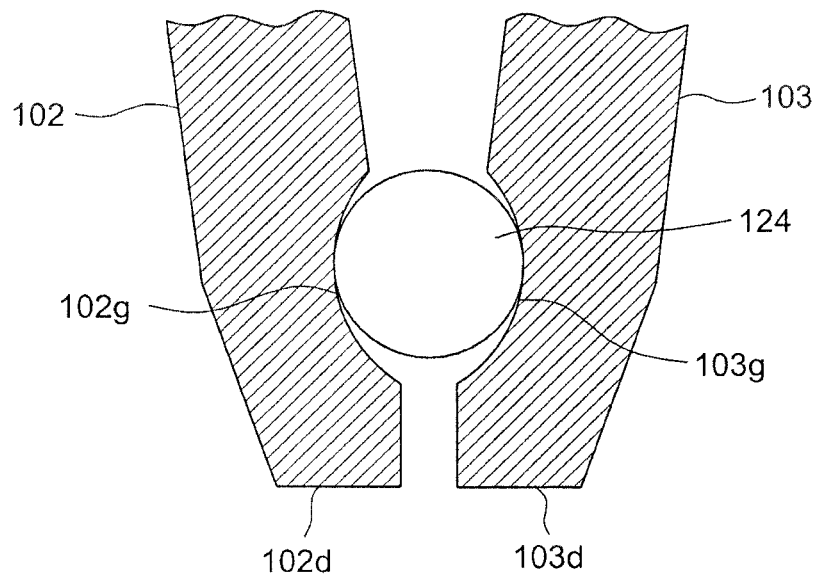
Figure 9:
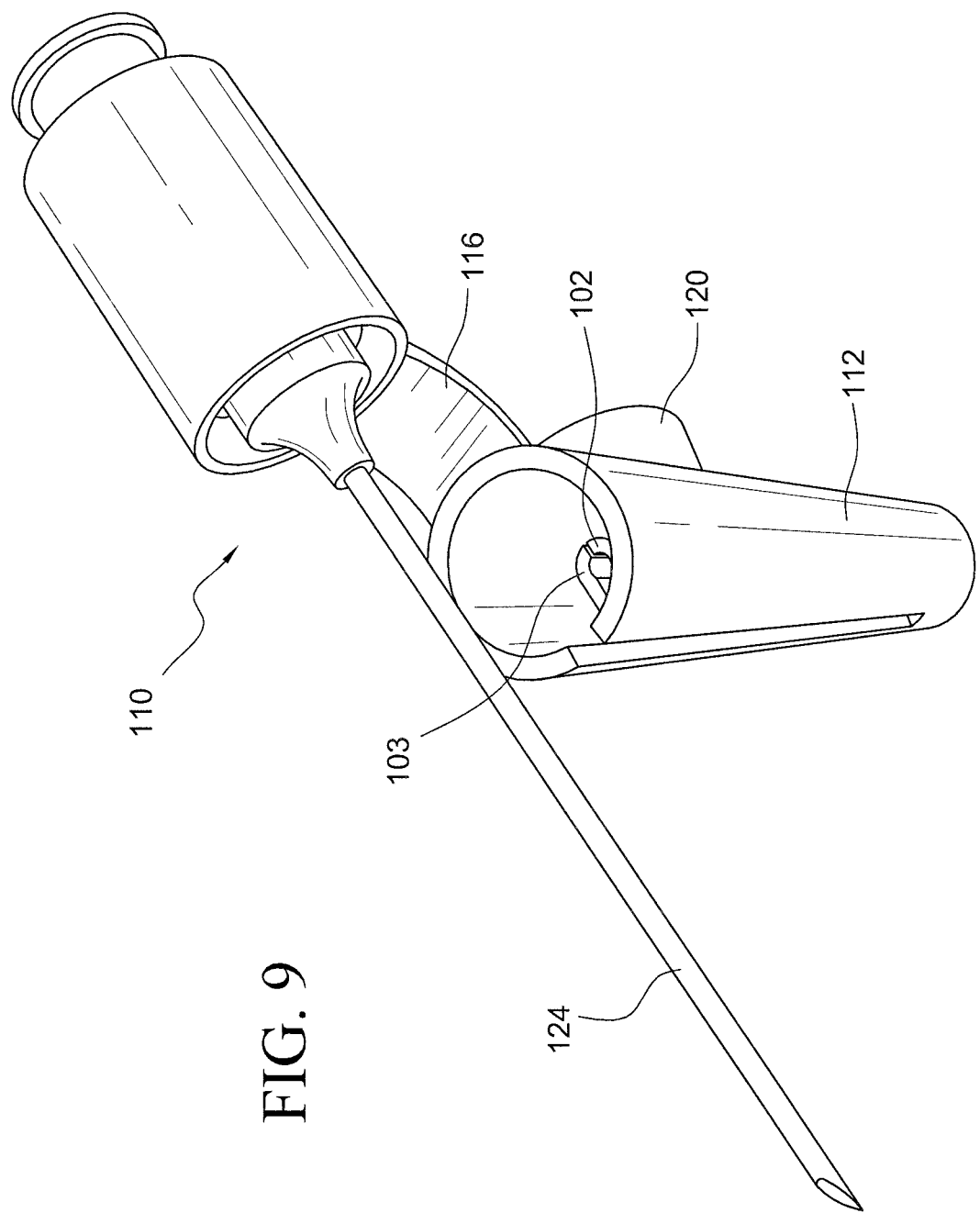
Figure 10:
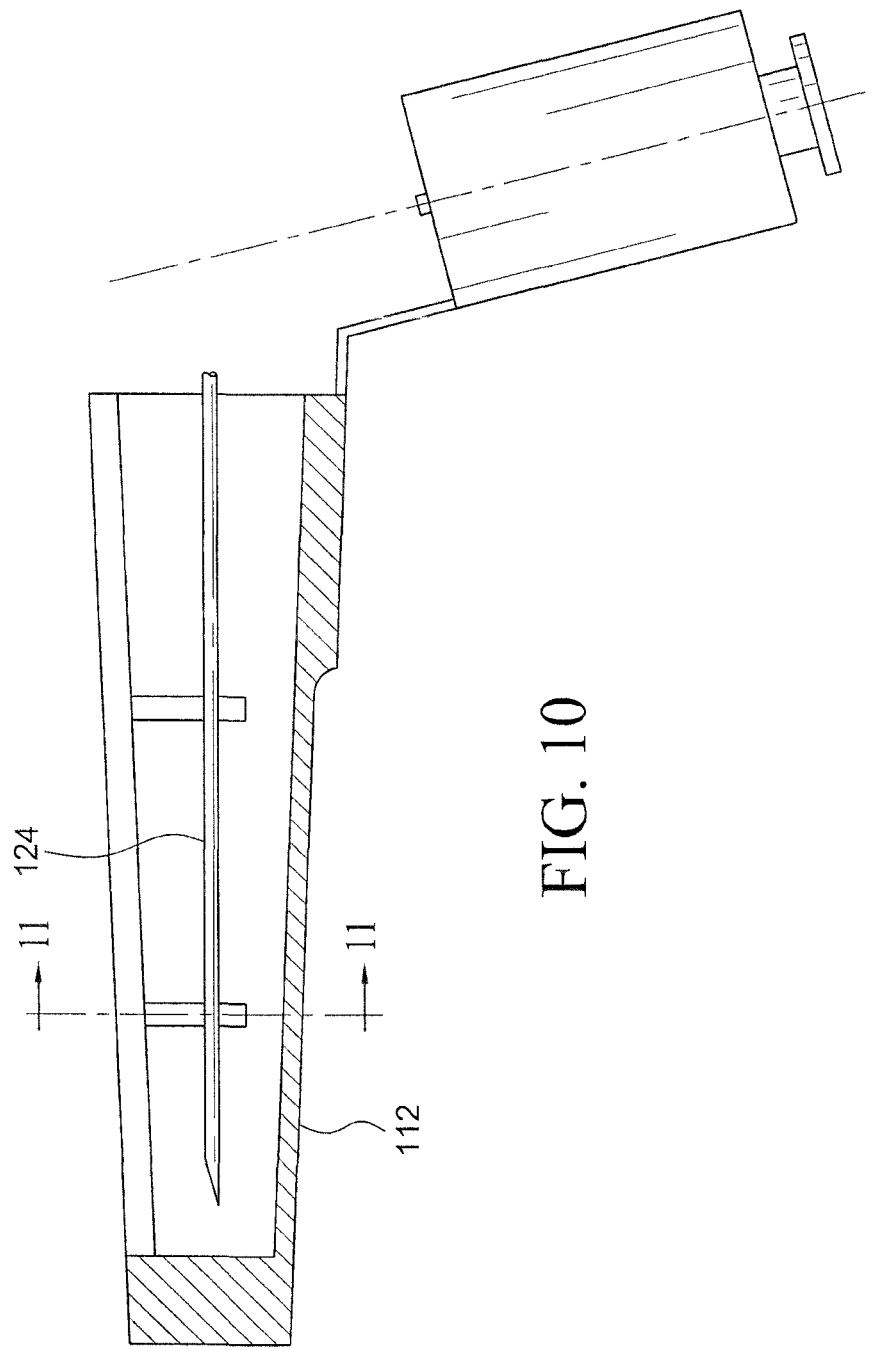
Figure 11:
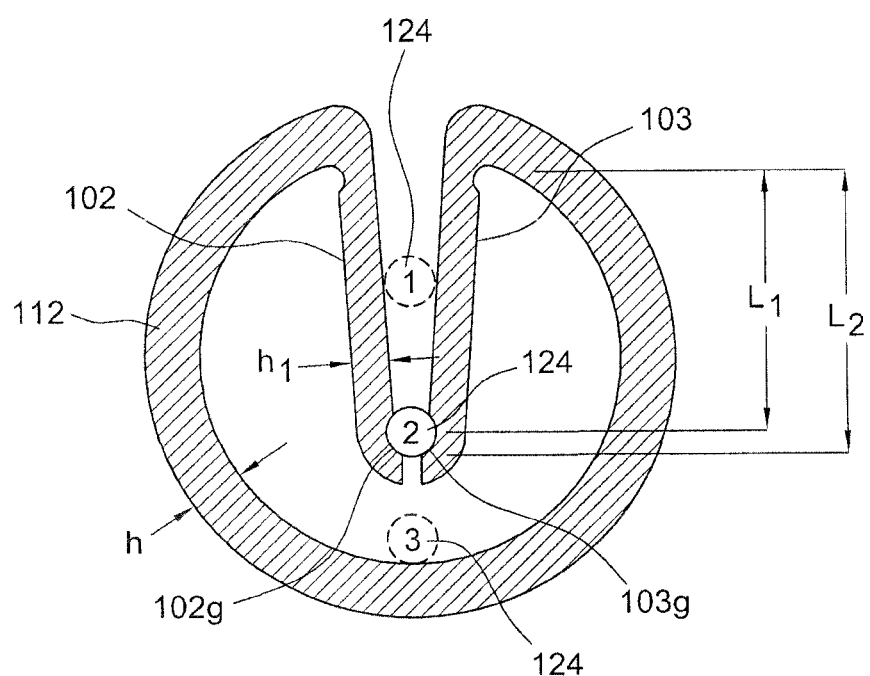

The first embodiment is shown with reference to FIGS. 8 to 12. FIGS. 8A and 8B are cross-sectional views of the distal shield member 112 of the needle stick protection device 110. In accordance with this embodiment the distal shield member 112 is square shaped. FIGS. 9, 10, and 11 show an alternative embodiment with a circular shaped distal shield member. FIGS. 12A, 12B, and 12C show various views of yet another embodiment. As these embodiments are similar, similar reference numerals have been used were appropriate. Various shapes are shown as being used in conjunction with the shield member, and it is appreciated the exact shape thereof may be varied without departing form the spirit of the present invention.

These various embodiments disclose a distal shield member 112 in which the needle 124 is captured between two cantilevered beams 102, 103. With reference in particular to FIGS. 8A and 11, the needle 124 passes from Position 1 (where it is not shielded), to Position 2 (where it is shielded and locked between the two cantilevered beams 102, 103), and ultimately to Position 3 (where it is rendered irreversibly locked out and within the interior space defined by the distal shield member 112). It should be noted that while two beams are provided in these embodiments, it is appreciated any number of cantilevered beams may be present inside of the distal shield member.

In accordance with the disclosed embodiment, inside of the distal shield member 112 are two radially oriented symmetrical cantilevered beams 102, 103 that are oriented approximately 5 degrees off the centerline of the entry (that is, the slot of the distal shield member 112) position of the hypodermic needle 124 into the distal shield member 112. While a 5 degree offset is disclosed in accordance with a disclosed embodiment, the exact orientation may be varied slightly without departing from the spirit of the present invention. In Position 1, the needle 124 is inside the distal shield member 112 of the needle stick protection device 110, just touching the cantilevered beams 102, 103 and not locked. In Position 2, the needle 124 falls into a circular opening within the beams 102, 103 and is locked in a safe position. In Position 3, the needle 124 has passed through the cantilevered beams 102, 103 and is no longer removable, and is "locked out."

The cantilevered beams 102, 103 have ground out areas (or concave recesses) 102g, 103g within the cantilevered beams 102, 103 of which the diameter defined by the ground out area 102g, 103g is slightly larger than the needle diameter. The distal end 102d, 103d of each of the cantilevered beams 102, 103 is a flat end. Passage of the needle 124 from the ground out portion 102g, 103g between the cantilevered beams 102, 103 where it is effectively shielded and held between the beams 102, 103 and back to a position offering use of the needle can be accomplished an infinite amount of times. As such, the two cantilevered beams 102, 103 are of sufficient durometer to allow slight separation as the needle 124 slides inward between the two cantilevered beams 102, 103 to facilitate passage of the needle 124. The straight distal ends 12d, 103d of the cantilevered beams 102, 103 result in an impermeable face to prevent re-passage of the needle 124 between the cantilevered beams 102, 103 once the needle 124 is moved to Position 3; thusly resulting in a permanent lock out for disposal of the device.

Discussion of the use and mechanism of this embodiment is now in order. The needle stick protection device 110 is again operated in a manner similar to the aforementioned embodiment, that is, it contains a proximal base member 114 and distal shield member 112, that are connected by a living hinge 116. The syringe and hypodermic needle 124 are attached in a similar fashion as described earlier, being mated to a syringe and a hypodermic needle 124. After using the hypodermic needle 124 and wishing protection from a needle stick from a contaminated needle 124, the operator pushes on the shield actuating tab 120 downwards towards the hypodermic needle 124. In this embodiment, the first click or position, noted as Position 2 where the needle 124 is between the cantilevered beams 102, 103 and within the ground out portions 102g, 103g, allows the needle 124 to be "SAFE," yet opened to be used again. Further pushing down results in a second, more pronounced click in which the needle 124 enters Position 3 when it has moved beyond the cantilevered beams 102, 103 and is held within the void defined by the inner wall of the distal shield member 112, where it cannot be used again, and is successfully "LOCKED OUT."

In Position 2, the needle 124 may be held under a constant beam load by letting the cantilevered beams 102, 103 bend slightly. The needle 124 may also be free, that is, fitting it into the cantilevered beams 102, 103 with a small radial clearance between the needle 124 and the circular portions in the cantilevered beam 102, 103. Leaving a small radial clearance will prevent the cantilevered beams 102, 103 from "creep," which will gradually lower the radial force on the needle 124. To reach the "LOCK OUT" Position 3 as seen in FIG. 8, the needle 124 is forced out of Position 2 by separating the two cantilevered beams 102, 103 far enough to let the needle 124 enter Position 3, which does not allow further use of the needle stick protection 110 device by blocking reentry into Position 2. The needle stick protection device 110 can now be safely disposed of as is conventional for medical waste, without injury to clean-up personnel.

Figure 13:
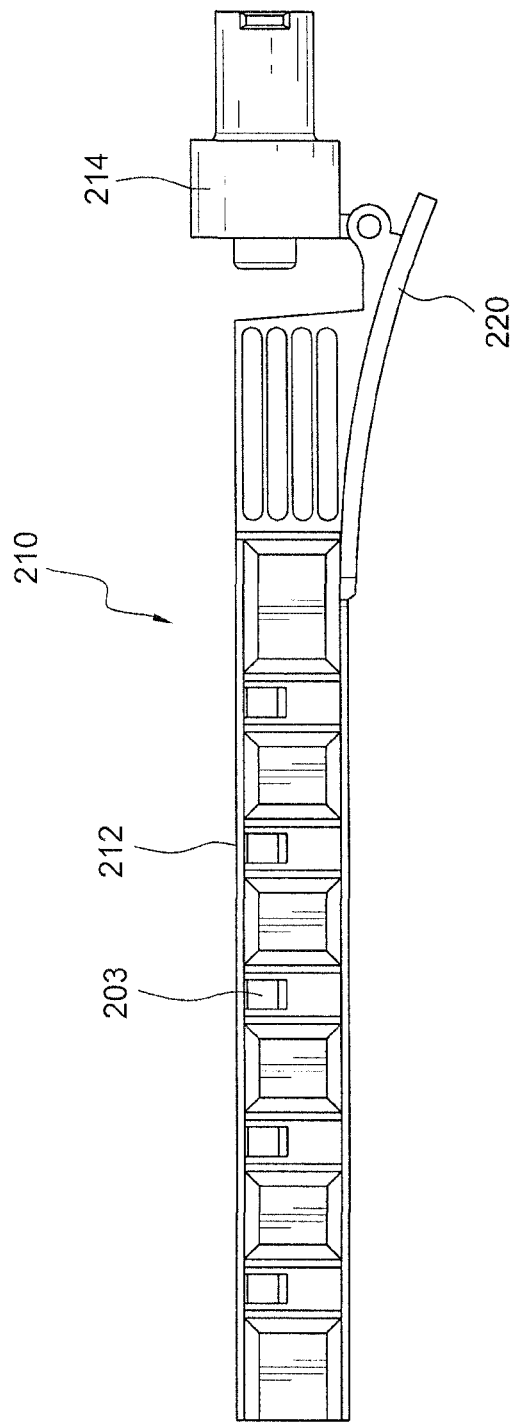
FIGS. 13 to 15 illustrate an alternative embodiment distal shield member utilizing inner projecting beams in which two cantilevered beams are directly opposed to each other.
Figure 14:
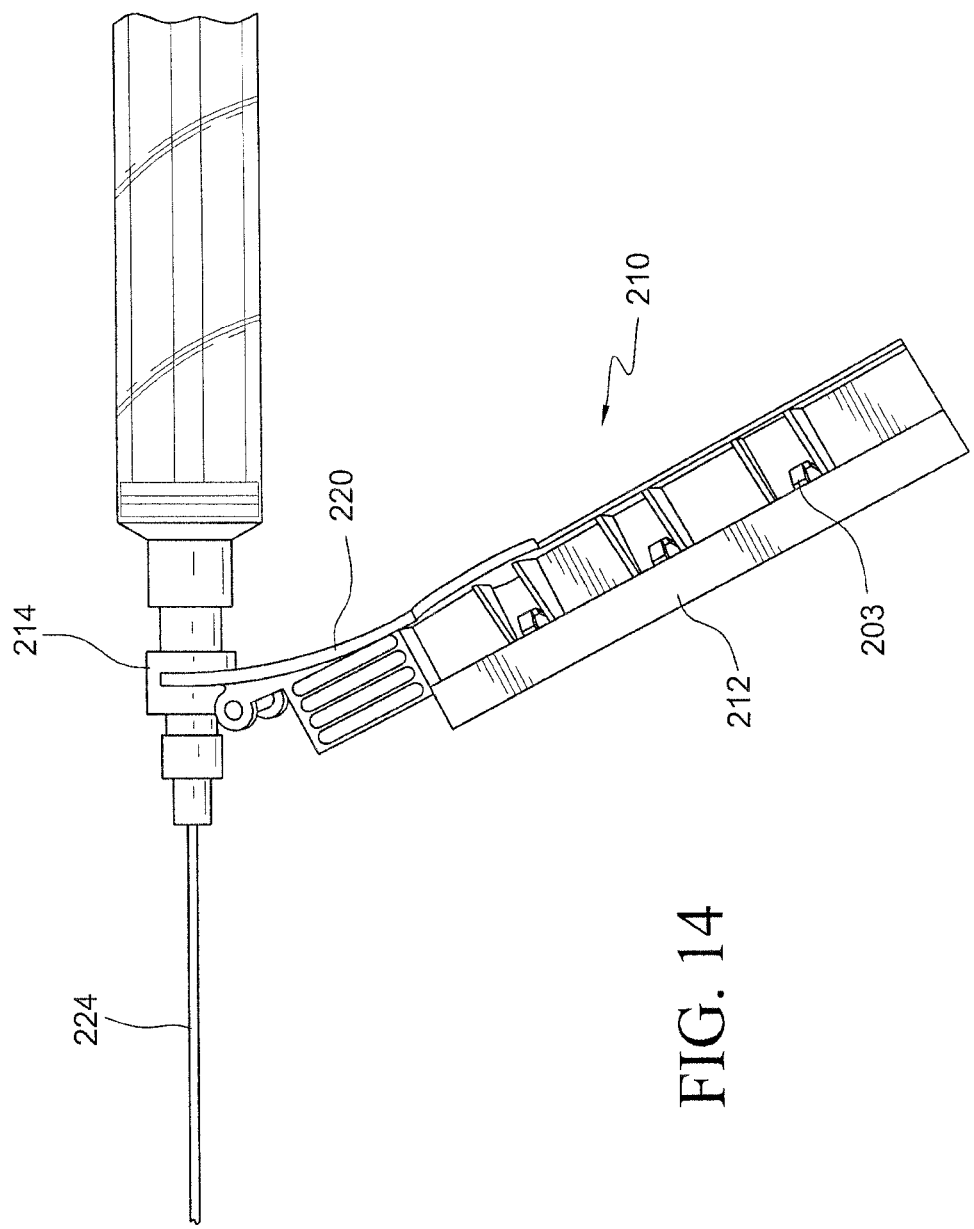
Figure 15:
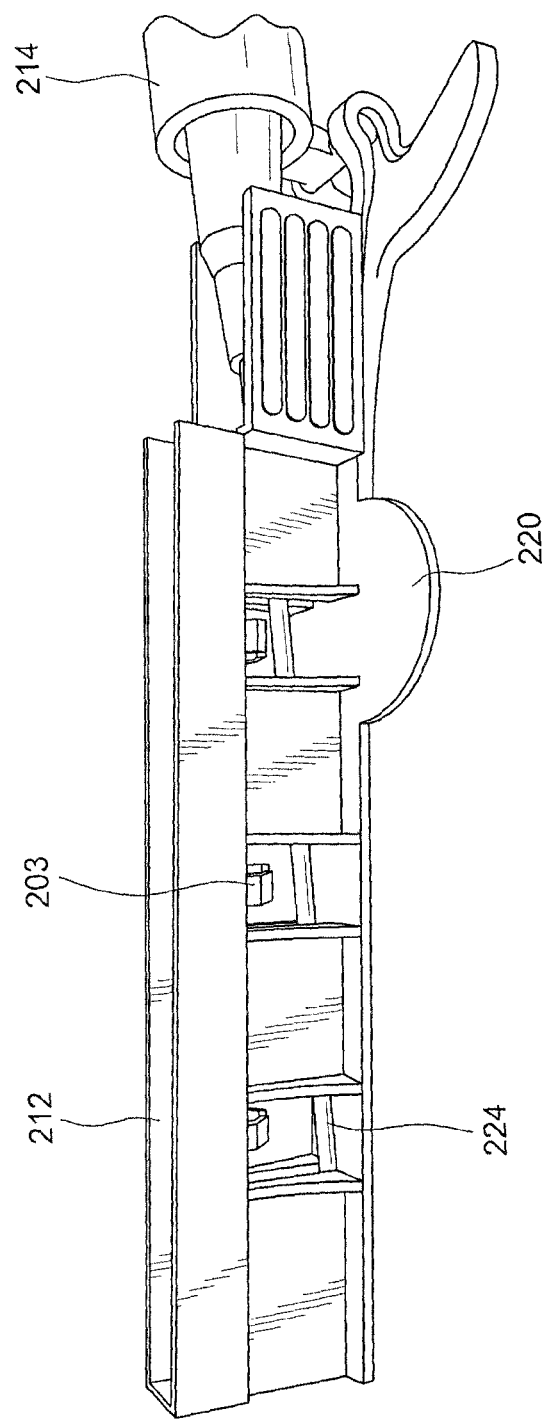

An alternative embodiment as seen in FIGS. 13 to 15 discloses a needle stick protection device 210 composed of a proximal base member 214 containing the Luer connections as described above, and a distal shield member 212 containing internal cantilevered beams 202, 203 that serve as a locking mechanism permitting continued use and safe shielding, as well as a final "LOCK-OUT" mechanism in accordance with the embodiment disclosed with reference to FIGS. 8 to 12. This embodiment employs multiple V shaped internal cantilevered beams 202, 203 located on the inner aspect of the shield member 212, which result in gripping of the needle 224 when in the safety, able to reuse position.

The internal cantilevered beams 202, 203 contained within the distal shield member 212 act in a similar fashion as the aforementioned embodiment in that the hypodermic needle 224 passes from a Position 2, where the needle 224 is safely grasped by the internal cantilevered beams 202, 203 to a final, end "LOCK-OUT" Position 3, where the needle 224 can no longer be used. The mechanism of action is similar to the aforementioned embodiments shown with reference to FIGS. 8 to 12. Again, by depressing the shield actuating tab 220, the needle 224 is depressed into the distal shield member 212, where it snaps into the multiple pairs of internal cantilevered beams 202, 203. Further depressing the shield actuating tab 220 results in the needle 224 passing into Position 3, where it becomes "LOCKED OUT", and can no longer be used. The internal cantilevered beams 202, 203 in this embodiment arise from the side walls of the distal shield portion, and are generally oriented in a downward fashion as it extends inward.

The base of each internal cantilevered beam 202, 203 is attached into the side wall of the needle housing body, or distal portion of the needle stick protection device 210. Each internal cantilevered beam 202, 203 then extends inward, and is angled downward. A semicircular design is incorporated into the base of the internal cantilevered beam 202, 203, which supports and grabs onto the needle with frictional force. Further pressure on the outside of the needle stick protection device 210 from this position pushes the hypodermic needle 224 past the two angled portions of the internal cantilevered beam 202, 203, with passage into the subsequent cavity, thereby permanently locking the needle stick protection device 210, preventing further use of the needle.

Figure 16:
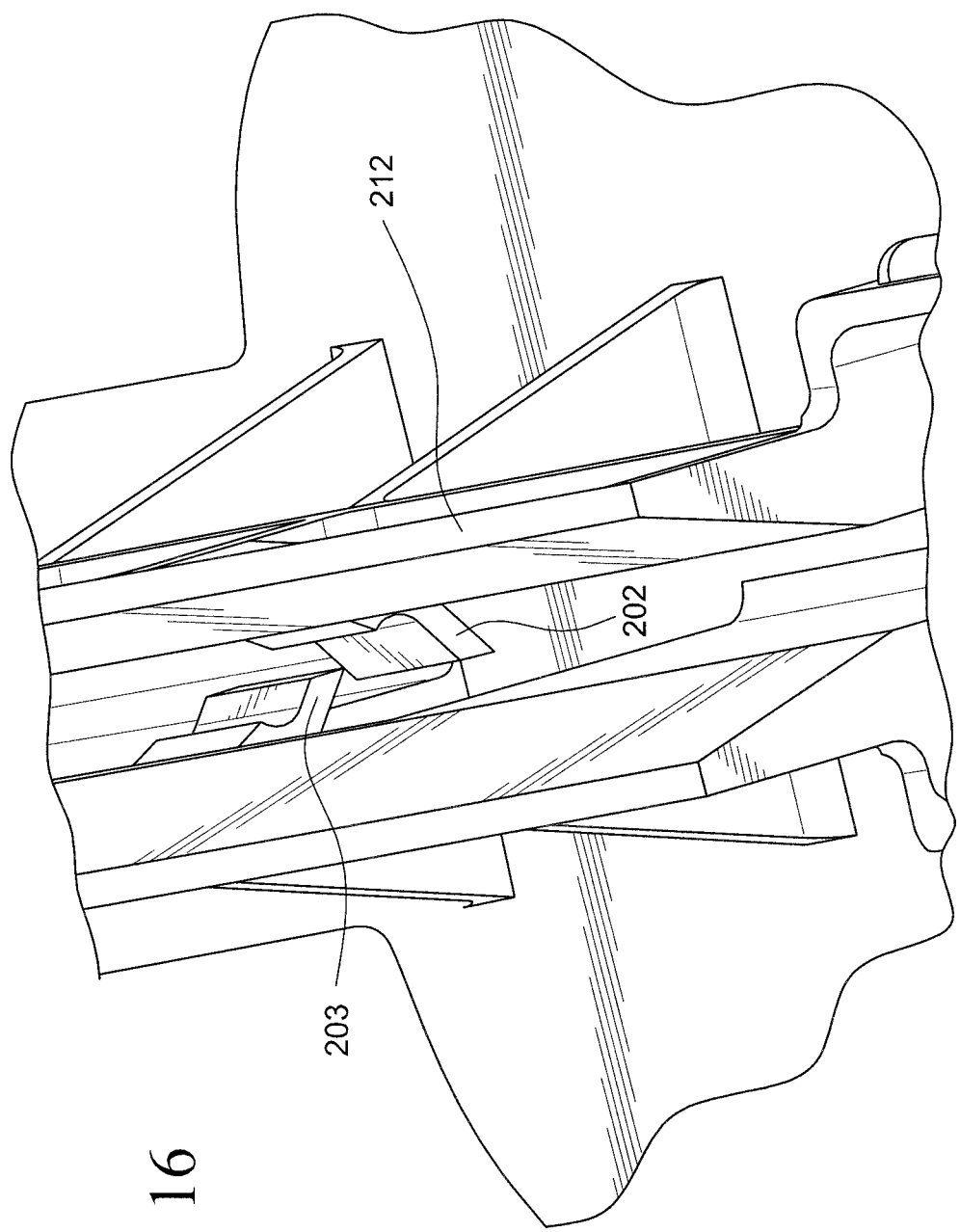
FIG. 16 is a highly detailed perspective view of an alternative embodiment of the distal shield member disclosed with reference to FIGS. 13 to 15 wherein the two cantilevered beams are staggered rather than aligned and directly opposed to each other.
Figure 17:
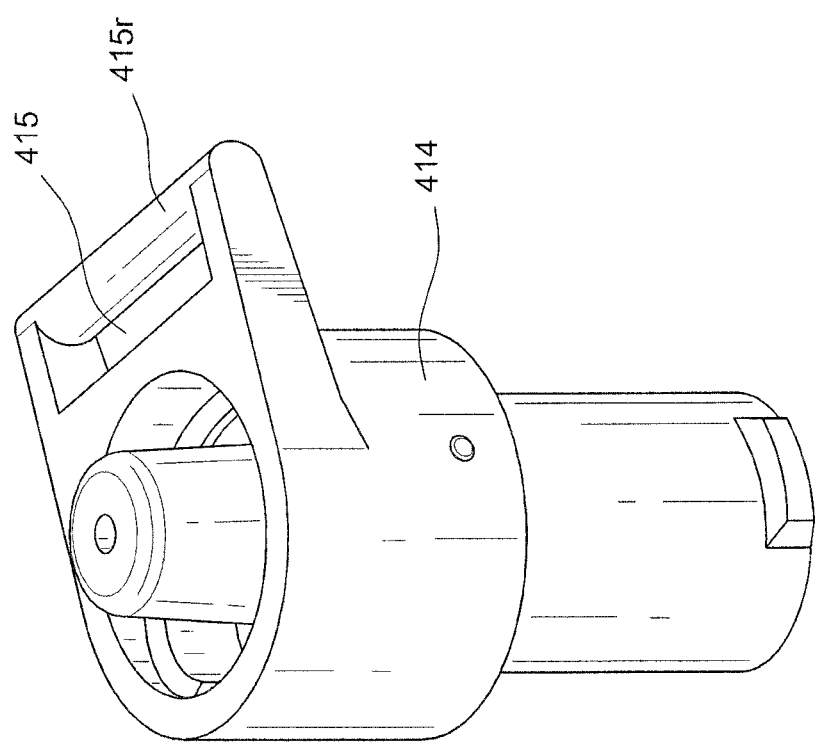
FIGS. 17, 18A, 18B, 19A and 19B demonstrate an alternative embodiment to the living hinge of the previously disclosed embodiment.

While opposed a beams are disclosed with reference to FIGS. 8 to 12 and 13 to 15, it is appreciated the beam members need not be directly opposed, but may be staggered as shown in FIG. 16. Staggering the internal cantilevered beams 202, 203 decreases the individual grip on the needle 224 exerted by each internal cantilevered beam 202, 203 necessitating the addition of more beams housed within the distal shield member 212 of the needle stick protection device 210.

It is noted that while all four different mechanisms of action embodiments described all can operate independently, the manufacturer may combine any combination of locking mechanism described above involving the base, or the inner shield locking mechanism, as one does not preclude the addition of another embodiment.

Alternative embodiments obviating the use of the living hinge can be used for all three embodiments of the above needle stick protection device. These are depicted in FIGS. 18 to 20.

Figures 18A, 18B:
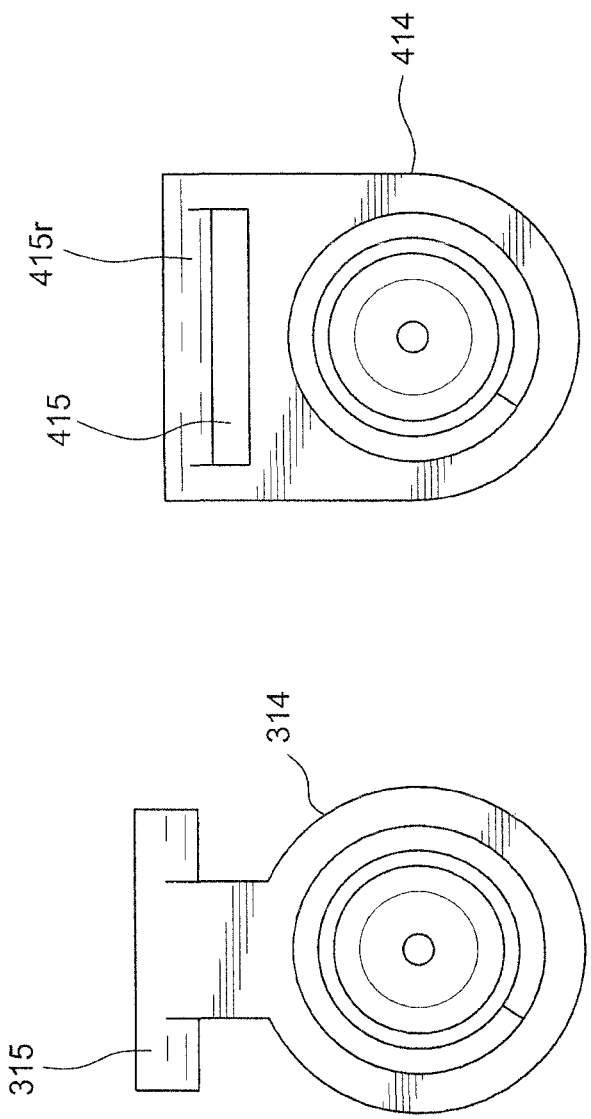
Figure 19A:
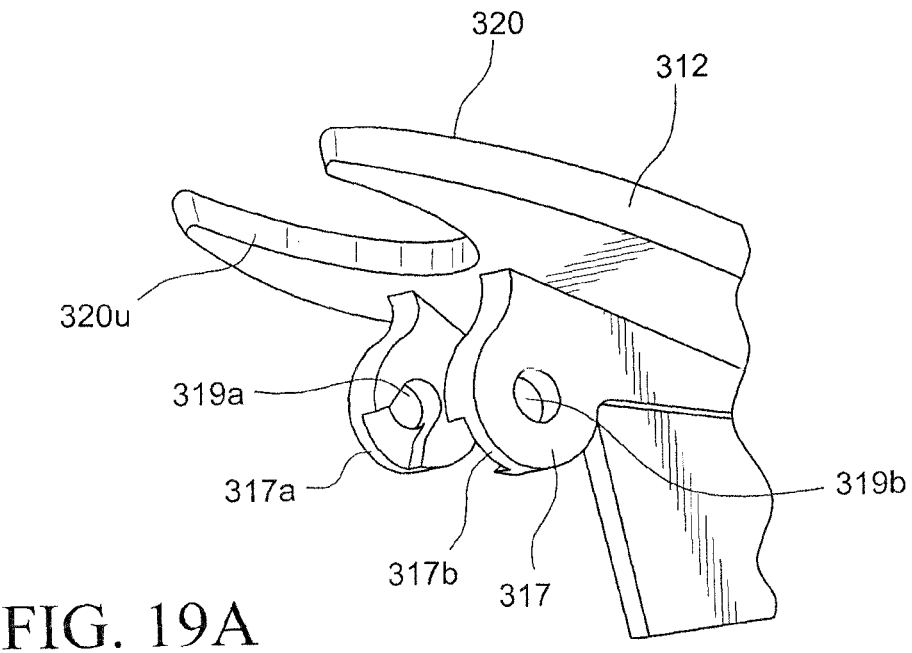

Two different hinge mechanisms are presented. These are seen in FIGS. 18A, 18B, 19A and 19B. FIG. 18A shows a longitudinal bar 315 on a base of the proximal base member 314, while FIG. 18B describes an elevated portion with a carved out central slot 415 on a base of the proximal base member 414, essentially creating a horizontal rod.

The longitudinal bar 315 of the proximal base member 314 shown in FIG. 18A interacts with the distal portion 317 of the distal shield member 312 which has two curved clips 317a, 317b (see FIG. 19A) that latch onto the longitudinal bar 315, allowing full range of motion greater than a living hinge. In accordance with this embodiment, the bar 315 defines a structure that can be viewed in cross section as a "T," and the mechanism is described as a "longitudinal bar on a base." The right and left ends of the "T" defined by the bar 315 fit into two holes 319a, 319b on the curved clips 317a, 317b of the distal shield member 312 of the needle stick protection device.

Figure 19B:
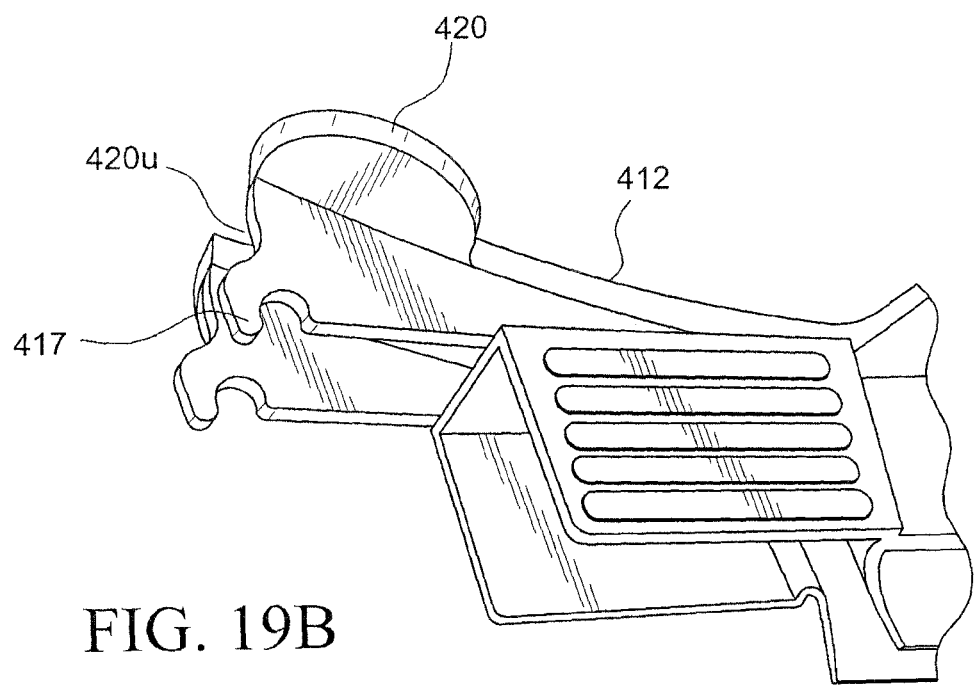
Figure 20:
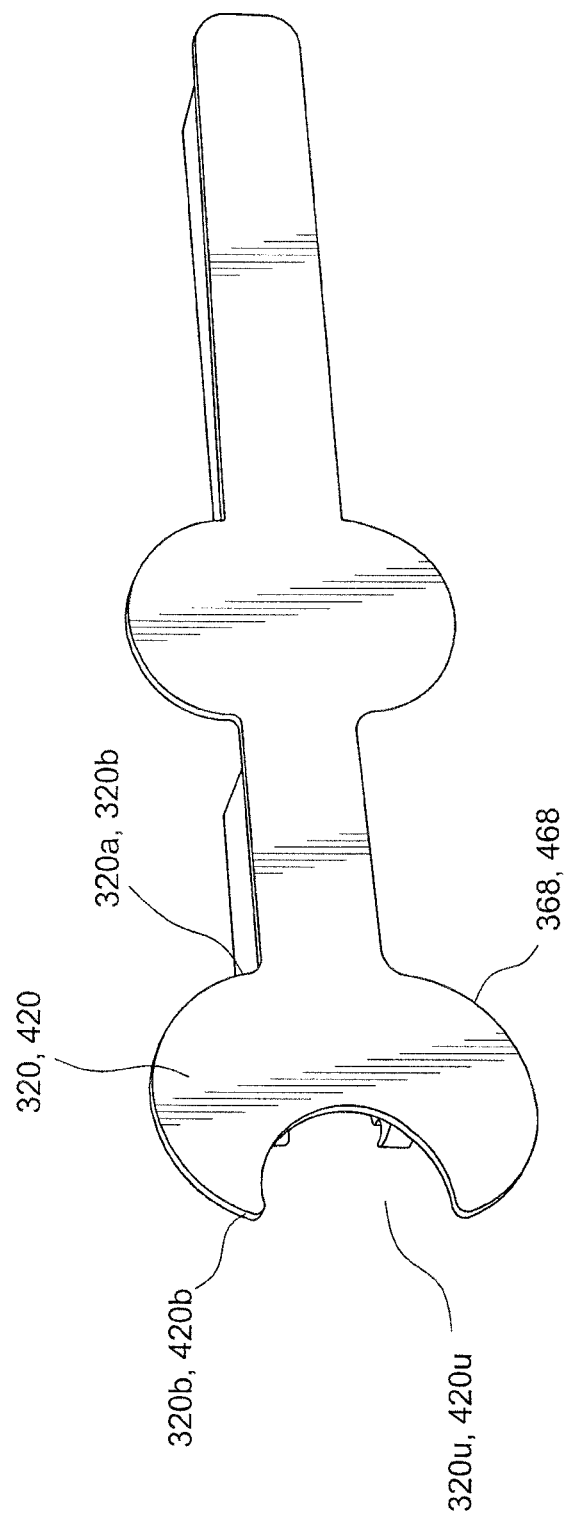
FIG. 20 is a top view showing the "U" shaped finger tab design in accordance with the embodiments disclosed with reference to FIGS. 17, 18A, 18B, 19A and 19B.

The second alternative to the living hinge as shown in FIGS. 18B and 19B, includes curved clips 417 that snap onto the central slot 415 of the proximal base member 414, with the curved clips 417 latching onto the horizontal bar 415r defined by the slot 415, with the carved out central slot 415 allowing rotation of the distal shield member 412 by rotation of the curved clips 417 along the axis of the horizontal rod. This embodiment is described as an "elevated rod with carved out central slot," wherein the bar 415 mates via curved clips 417 on the distal end of the distal shield member 412, to result in hinge motion.

It should be noted that both novel approaches to the living hinge are incorporated into the base of the raised shield tab 320, 420 actuation portion of the distal portion of the distal shield member 312, 412. A full range of motion is ensured in accordance with the embodiments disclosed in FIGS. 18A, 19A, 18B and 19B by forming the shield actuating tab 320, 420 with a U-shaped cutout (or opening) 320u, 420u (see FIG. 20). In particular, and considering the shield actuating tab 320, 420 is located adjacent the hinge 316, 416 adjacent the second end 368, 468 of the distal shield member 312, 412, rotation of the distal shield member 312, 412 brings the shield actuating tab closer to the proximal base member 314, 414. This limits the range of motion that the distal shield member 312, 412 can move relative to the proximal base member 314, 414. By removing a portion of the shield actuating tab 320, 420 that faces the proximal base member 314, 414 (that is, the shield actuating tab 320, 420 along the second end 320b, 340b thereof as opposed to the first end 320a, 420a of shield actuating tab 320, 420 that faces the first end of distal shield member 312, 414) the additional range of motion is achieved. The best range of motion is evidenced when a "U" shaped cutout is placed on the shield actuating tab 320, 420 of the distal shield member 312, 412. By creating this "U" shaped cutout and in conjunction with the novel hinge designs, the distal shield member 312, 412 of the needle stick protection device can now swing in approximately 145 degrees of arc, greater than the 90 degrees seen with a standard living hinge.

Regardless of the embodiment employed, the present needle stick protection device produces a multi-use needle stick protection device with a distal shield member that can be used, then placed in a safe locked position innumerable cycles during a procedure. As such, the present needle stick protection device can be provided to replace the standard needle cap, providing safety prior to initial use during a procedure, and a lock out mechanism to facilitate safe needle disposal. The needle stick protection device can be locked so it cannot be used again, and is safe for disposal by rotating a rotating lock shield on the outer aspect of the distal shield member. The rotating lock shield turns to physically obstruct the slot that allows needle passage through the distal shield member to result in permanent lockout.

While the preferred embodiments have been shown and described, it will be understood that there is no intent to limit the invention by such disclosure, but rather, is intended to cover all modifications and alternative constructions falling within the spirit and scope of the invention.

The invention claimed is:

1. A needle stick protection device, comprising:
 a distal shield member including a slot which allows a needle to freely pass between shielded and unshielded positions for multiple cycles of shielding and unshielding, the distal shield member includes first and second cantilevered beams between which the needle may be retained;
 a proximal base member;
 a hinge connecting the distal shield member to the proximal base member; and
 a locking mechanism securing the proximal base member to the distal shield member;
 wherein the distal shield member includes a distal rotating shield adapted for rotation and locking to prevent further use of the needle stick protection device, whereby rotation of the distal rotating shield selectively blocks the slot that allows passage of the needle in and out of the needle stick protection device.

2. A needle stick protection device, comprising:
 a distal shield member including a shield having a slot which allows a needle to freely pass between shielded and unshielded positions, the distal shield member further includes a distal rotating shield adapted for rotation and locking to prevent further use of the needle stick protection device, whereby rotation of the distal rotating shield selectively blocks the slot that allows passage of the needle in and out of the needle stick protection device;
 a proximal base member; and
 a hinge connecting the distal shield member to the proximal base member;
 wherein the distal shield member includes a compressive cylindrical sleeve and the proximal base member includes a cylindrical collar, the compressive cylindrical sleeve including an open portion that is slightly smaller than a diameter of the cylindrical collar allowing the compressive cylindrical sleeve to move over the cylindrical collar.

3. The needle stick protection device according to claim 2, wherein the rotating lock shield includes a wedge and the shield includes a raised flange that interacts with the wedge to close off the slot and ultimately lock the rotating lock shield relative to the shield.

4. The needle stick protection device according to claim 3, wherein the wedge rotates with the rotating lock shield.

5. The needle stick protection device according to claim 3, wherein the wedge is an angled wedge.

6. The needle stick protection device according to claim 3, wherein the raised flange includes a locking cavity in which the wedge is passed when it is desired to close off the slot and ultimately lock the rotating lock shield relative to the shield.

7. The needle stick protection device according to claim 2, further including a shield actuating tab placed on the distal shield member to assist in one finger use of the needle stick protection device.

8. The needle stick protection device according to claim 2, wherein the rotating lock shield includes a slot which extends from a first end thereof to a second end thereof.

9. The needle stick protection device according to claim 2, wherein the distal shield member includes first and second cantilevered beams between which the needle may be retained.

10. The needle stick protection device according to claim 9, wherein the first and second cantilevered beam are aligned.

11. The needle stick protection device according to claim 9, wherein the first and second cantilevered beams are staggered.

12. The needle stick protection device according to claim 9, wherein the first and second cantilevered beams are radially oriented off a centerline of the slot of the distal shield member.

13. The needle stick protection device according to claim 9, wherein each of the first and second cantilevered beams includes a concave recess.

14. The needle stick protection device according to claim 2, wherein the compressive cylindrical sleeve has an inner diameter equal to an outer diameter of the cylindrical collar.

* * * * *